United States Patent
Poland

(10) Patent No.: US 12,059,298 B2
(45) Date of Patent: Aug. 13, 2024

(54) ACQUISITION WORKFLOW AND STATUS INDICATORS IN A HANDHELD MEDICAL SCANNING DEVICE

(71) Applicant: KONINKLIJKE PHILIPS N.V., Eindhoven (NL)

(72) Inventor: McKee Dunn Poland, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 150 days.

(21) Appl. No.: 17/260,438

(22) PCT Filed: Jul. 10, 2019

(86) PCT No.: PCT/EP2019/068466
§ 371 (c)(1),
(2) Date: Jan. 14, 2021

(87) PCT Pub. No.: WO2020/016069
PCT Pub. Date: Jan. 23, 2020

(65) Prior Publication Data
US 2021/0282747 A1    Sep. 16, 2021

Related U.S. Application Data

(60) Provisional application No. 62/699,928, filed on Jul. 18, 2018.

(51) Int. Cl.
*A61B 8/08* (2006.01)
*A61B 8/00* (2006.01)

(52) U.S. Cl.
CPC ............ *A61B 8/4455* (2013.01); *A61B 8/085* (2013.01); *A61B 8/42* (2013.01); *A61B 8/4427* (2013.01); *A61B 8/462* (2013.01); *A61B 8/565* (2013.01)

(58) Field of Classification Search
CPC ......... A61B 8/4455; A61B 8/085; A61B 8/42; A61B 8/4427; A61B 8/462; A61B 8/565
See application file for complete search history.

(56) References Cited

U.S. PATENT DOCUMENTS

| | | | | |
|---|---|---|---|---|
| 5,897,498 A | * | 4/1999 | Canfield, II | G01S 7/003 600/437 |
| 8,672,851 B1 | * | 3/2014 | Quirk | A61B 8/4218 600/459 |

(Continued)

FOREIGN PATENT DOCUMENTS

| | | |
|---|---|---|
| WO | 2018035392 A1 | 2/2018 |
| WO | 2018091337 A1 | 5/2018 |

OTHER PUBLICATIONS

International Search Report and Written Opinion for International Application No. PCT/EP2019/068466, filed Jul. 10, 2019, 14 pages.

*Primary Examiner* — Alexei Bykhovski

(57) ABSTRACT

In an embodiment, a handheld ultrasound scanning device is disclosed. One embodiment of the handheld ultrasound scanning device comprises a housing configured for handheld use, an ultrasound assembly at least partially disposed within the housing and configured obtain ultrasound data, a display unit at least partially disposed within the housing and comprising a display, and a processor disposed within the housing, wherein the processor is in communication with the ultrasound assembly and the display unit. The processor operable to receive a selection of an anatomical structure to be scanned with the ultrasound assembly, receive ultrasound data from the ultrasound assembly, determine whether the received ultrasound data includes data representative of the anatomical structure, and output an indication to the display unit in response to the determining.

20 Claims, 9 Drawing Sheets

(56) References Cited

U.S. PATENT DOCUMENTS

| | | |
|---|---|---|
| 2005/0251013 A1 | 11/2005 | Krishnan et al. |
| 2009/0093719 A1 | 4/2009 | Pelissier et al. |
| 2010/0036248 A1* | 2/2010 | Chouno ............... A61B 8/08 600/443 |
| 2010/0277305 A1* | 11/2010 | Garner ............... A61B 8/4438 340/539.1 |
| 2012/0051614 A1 | 3/2012 | Olszewski et al. |
| 2013/0190600 A1 | 7/2013 | Gupta et al. |
| 2015/0133784 A1 | 5/2015 | Kapoor et al. |
| 2017/0000453 A1* | 1/2017 | Feltovich ............ A61B 8/0866 |
| 2017/0086785 A1 | 3/2017 | Bjaerum |
| 2017/0360412 A1* | 12/2017 | Rothberg ............ G06T 19/006 |
| 2018/0344286 A1* | 12/2018 | Mienkina ............ G16H 40/63 |
| 2019/0192114 A1* | 6/2019 | Mauldin, Jr. ........ A61B 8/5207 |

\* cited by examiner

ACQUISITION WORKFLOW AND STATUS INDICATORS IN A HANDHELD MEDICAL SCANNING DEVICE

RELATED APPLICATIONS

This application is the U.S. National Phase application under 35 U.S.C. § 371 of International Application No. PCT/EP2019/068466, filed on Jul. 10, 2019, which claims the benefit of and priority to Provisional Application No. 62/699,928, filed Jul. 18, 2018, which is incorporated by referenced in its entirety.

TECHNICAL FIELD

The present disclosure relates generally to handheld medical scanning devices and, in particular, to a handheld medical scanning device configured to selectively store relevant imaging data, discard irrelevant imaging data, and to provide guidance to a user during imaging.

BACKGROUND

As medical technology has advanced over the years, several different imaging modalities, e.g., magnetic resonance imaging (MRI), computed tomography (CT), x-ray, fluoroscopy, angiography, ultrasound, etc., have been developed to allow physicians to view anatomical structures within a patient's body without having to open the patient surgically. In the case of ultrasound, ultrasonic waves are emitted from ultrasonic transducers into the patient's body. The ultrasonic waves are partially reflected by discontinuities arising from tissue structures, red blood cells, and other features within the patient. Echoes from the reflected waves are received by the ultrasonic transducers and processed to produce an ultrasonic image. The ultrasonic image is generally outputted to a display for viewing by a physician. Review of the displayed images often plays an integral role in a physician's diagnosis and treatment plan.

SUMMARY

Aspects of the present disclosure provide ultrasound data acquisition feedback and/or data assessment feedback without actually generating and displaying an ultrasound image to the user of the ultrasound scanning device or only displaying fewer, selected, and/or more relevant ultrasound images. Advantageously, omitting and/or minimizing ultrasound image display lessens the processing and/or memory hardware requirements for the ultrasound scanning device while still providing helpful directions and/or assessment output to, e.g., a novice ultrasound operator or a patient.

For example, embodiments of the present disclosure provide improved systems and methods for storing imaging data on a handheld medical scanning device. In that regard, the present disclosure provides for a handheld medical scanning device configured to automatically segregate relevant imaging data from irrelevant imaging data based on a selected imaging procedure, e.g., a bladder volume measurement procedure. The handheld medical scanning device may be configured to store imaging data relevant to the selected imaging procedure in a local non-volatile memory and discard imaging data irrelevant to the selected imaging procedure. Storing only the relevant imaging data advantageously conserves memory resources and reduces the size of imaging data files. Accordingly, the teachings of the present disclosure advantageously increase the number of imaging data files the handheld medical scanning device is capable of storing.

Embodiments of the present disclosure further provide improved systems and methods for outputting guidance to a user to facilitate imaging of an anatomical structure. In that regard, the present disclosure provides for a handheld medical scanning device configured to analyze imaging data obtained by the handheld medical scanning device to determine whether the handheld medical scanning device is located at a suitable position to image the anatomical structure. Based on the analysis, the handheld medical scanning device is configured to output an indication either confirming that the handheld medical scanning device is suitably positioned or alerting the user to reposition the handheld medical scanning device. The handheld medical scanning device also provides an indication when imaging has been completed. These various indications advantageously increase the likelihood that useful imaging data will be obtained and reduce the likelihood that the user will remove the handheld medical scanning device before imaging is completed.

Embodiments of the present disclosure also provide improved systems and methods for assessing an anatomical structure. In that regard, the present disclosure provides for a handheld medical scanning device configured to obtain imaging data associated with an anatomical structure and output an assessment result to a display of the handheld medical scanning device without outputting an image of the anatomical structure to the display. Images of anatomical structures may be difficult for a non-medically trained user, such as a patient, to understand. Such users may find it easier to comprehend medical information presented in the form of assessment results, e.g., measurements and diagnoses. Accordingly, outputting an assessment result without outputting anatomical images advantageously reduces the likelihood that a non-medically trained user will become frustrated while using the handheld medical scanning device and increases the likelihood that such a user will understand the medical information displayed.

In one embodiment, a handheld ultrasound scanning device is disclosed. The handheld ultrasound scanning device comprises a housing configured for handheld use, an ultrasound assembly at least partially disposed within the housing and configured obtain ultrasound data, a display unit at least partially disposed within the housing and comprising a display, and a processor disposed within the housing, wherein the processor is in communication with the ultrasound assembly and the display unit. The processor is operable to: receive a selection of an anatomical structure to be scanned with the ultrasound assembly, receive ultrasound data from the ultrasound assembly, determine whether the received ultrasound data includes data representative of the anatomical structure, and output an indication to the display unit in response to the determining.

In some embodiments, the indication comprises an alert to reposition the handheld ultrasound scanning device when the ultrasound data received from the ultrasound assembly does not include data representative of the anatomical structure. In some embodiments, the processor is further operable to output an audible tone in response to the determining. In some embodiments, the processor is further operable to: communicate the received ultrasound data to a remote medical processing system. In some embodiments, the received ultrasound data is communicated to the remote medical processing system without an ultrasound image having been outputted to the display unit. In some embodiments, the processor is further operable to: receive, from the remote medical processing system, an assessment result, and output the assessment result to the display unit. In some embodiments, the processor is further operable to: generate an assessment result based on the ultrasound data received from the ultrasound assembly, and output the assessment result to the display unit. In some embodiments, the processor is further operable to: determine whether a scanning procedure has been completed, and output a second indication to the display unit in response to determining that the scanning procedure has been completed. In some embodiments, the processor is further operable to: determine whether an assessment of the anatomical structure has been completed, and output a third indication to the display unit in response to determining that the assessment of the anatomical structure has been completed. In some embodiments, the assessment of the anatomical structure comprises a measurement of the anatomical structure. In some embodiments, the ultrasound assembly comprises a miniaturized ultrasound assembly comprising a micro-beamformer.

In one embodiment, a method of ultrasound scanning is disclosed. The method of ultrasound scanning comprises receiving, by a processor disposed within a housing of a handheld ultrasound scanning device, a selection of an anatomical structure to be scanned with an ultrasound assembly at least partially disposed within the housing, receiving, by the processor, ultrasound data from the ultrasound assembly, and determining, by the processor, whether the ultrasound data received from the ultrasound assembly includes data representative of the anatomical structure. The method of ultrasound scanning further comprises outputting, by the processor, an indication to a display unit at least partially disposed in the housing and comprising a display in response to the determining.

In some embodiments, the method of ultrasound scanning further comprises communicating, by the processor, the received ultrasound data to a remote medical processing system. In some embodiments, the received ultrasound data is communicated to the remote medical processing system without an ultrasound image having been outputted to the display unit. In some embodiments, the method of ultrasound scanning further comprises determining, by the processor, whether a scanning procedure has been completed, and outputting, by the processor, a second indication to the display unit in response to determining that the scanning procedure has been completed. In some embodiments, the method of ultrasound scanning further comprises determining, by the processor, whether an assessment of the anatomical structure has been completed, and outputting, by the processor, a third indication to the display unit in response to determining that the assessment of the anatomical structure has been completed.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1A:
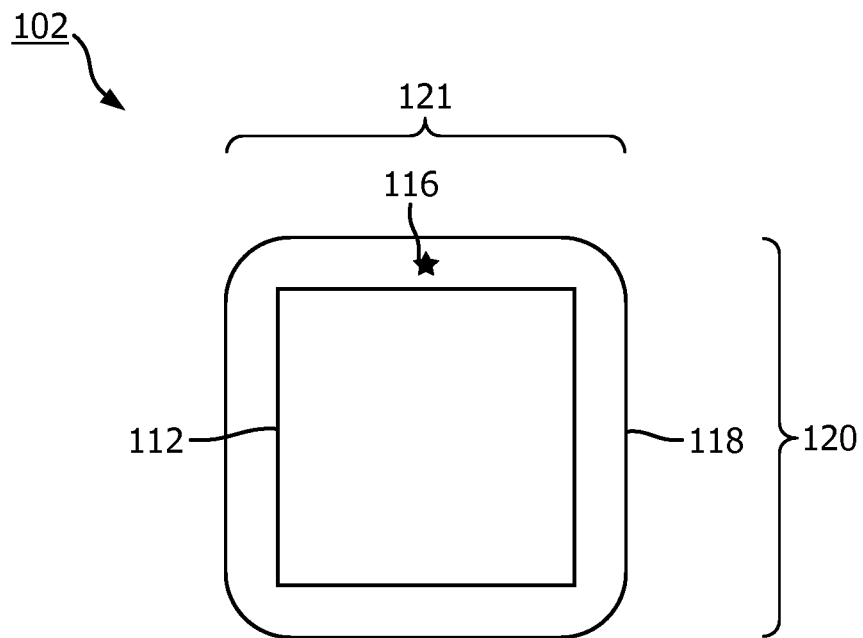
FIG. 1A is a diagrammatic top view of a handheld medical scanning device, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1B:
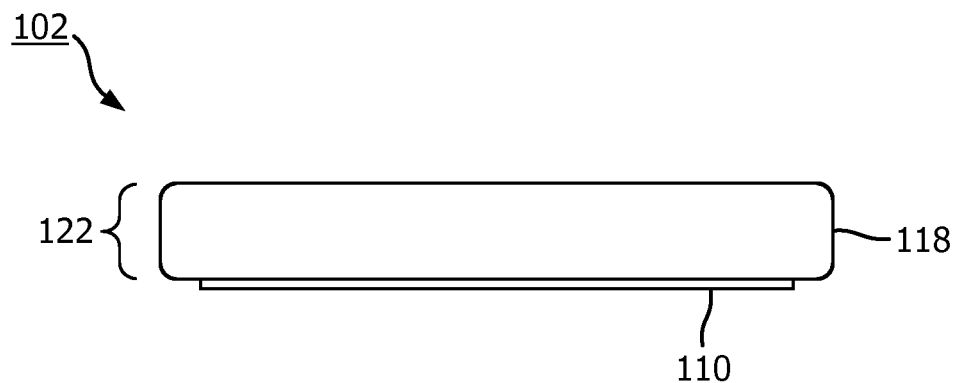
FIG. 1B is a diagrammatic side view of a handheld medical scanning device, according to aspects of the present disclosure.

Turning now to FIGS. 1A and 1B, shown therein are various diagrammatic views of a handheld medical scanning device 102, according to aspects of the present disclosure. As illustrated, the handheld medical scanning device 102 may include an imaging element 110, a display 112, a reference mark 116, and a housing 118. The housing 118 may have a length 120, width 121, and depth 122. The display 112 and the imaging element 110 may be disposed on top and bottom faces of the handheld medical scanning device 102, respectively, and may be wholly or partially disposed within the housing 118. Additional aspects of the handheld medical scanning device 102 and the various features thereof will be described in greater detail below.

The handheld medical scanning device 102 may be sized and shaped for handheld use. Though variously illustrated as having the perimeter of a square or rounded square, the handheld medical scanning device 102 may in some cases have a circular perimeter, a triangular perimeter, a rectangular perimeter, a pentagonal perimeter, a hexagonal perimeter, or a perimeter of some other shape. The housing 118 may have a length 120, width 121, and depth 122 suitable to enable a user to securely grip, with either hand or with both hands, the handheld medical scanning device 102 while imaging and/or other functions are performed. By way of particular example, but without limitation, the housing 118 may have a length 120 of seven centimeters, a width 121 of seven centimeters, and a thickness of two centimeters. Such dimensions would advantageously allow the handheld medical scanning device 102 to be used with a single hand grip by virtually all users. Users may be physicians, patients, or third parties, as the case may be.

A user may maintain a single hand grip on the handheld medical scanning device 102 by gripping the handheld medical scanning device 102 with their thumb on one lateral face of the housing 118 and their index finger on an opposing lateral face of the housing 118. The lateral faces may be thick enough, and the other dimensions small enough, that the most natural way to hold the handheld medical scanning device 102 is by its lateral faces. A user's hand may partially enclose the handheld medical scanning device such that the user's thumb, interdigital webbing, and forefinger touch three of the four sides of the handheld medical scanning device to form a comfortable grip. When the handheld medical scanning device 102 is held in this way, the display 112 may be viewable by a user while the imaging element 110 is pressed against a patient's body.

A reference mark 116 may be located on the housing 118. The reference mark 116 may help a user choose a grip on the handheld medical scanning device 102, e.g., a grip that will allow for convenient viewing of information shown on the display 112. For example, the user may know that the bottom of the display 112 is on the opposite side of the display 112 from the reference mark 116 and may choose a grip accordingly. The reference mark 116 may be particularly useful in guiding the user's choice of grip when the display 112 is powered off or blank. Inclusion of the reference mark 116 may advantageously reduce user frustration by reducing the likelihood that the user will desire a re-grip after initially gripping the handheld medical scanning device 102. The reference mark 116 may also serve as a reference relative to the imaging element 110, which may not be visible when placed against or adjacent to a patient's skin for imaging. In that regard, the reference mark 116 may advantageously assist a user in positioning the handheld medical scanning device 102 for imaging. The reference mark 116 may be sized so as to be conspicuous for reference purposes. The reference mark 116 may comprise an image, a logo, a brand, a symbol, a functional element, a speaker, a number, a letter, alphanumeric text, a signature, or combinations thereof. In some cases, the reference mark 116 may be tactile to facilitate its location by visually impaired users.

The display 112 may comprise a screen or monitor, which may comprise a capacitive or resistive touch screen, and may serve as a graphical user interface (GUI). In other instances, the display 112 may comprise one or more indicator lights, e.g., a red light and a green light. The display 112 may partially or wholly form a surface of the handheld medical scanning device 102. In any case, the display 112 may be part of a display unit. The display unit may comprise the display 112 and circuitry connecting the display 112 to a processor of the handheld medical scanning device 102. The display unit may be wholly or partially disposed within the housing 118.

The handheld medical scanning device 102 may be battery powered and may comprise one or more batteries. Said batteries may be disposed within the handheld medical scanning device 102 and may be removeable. In some instances, batteries powering the handheld medical scanning device 102 may be rechargeable. For example, the batteries of the handheld medical scanning device 102 may be recharged by mating the handheld medical scanning device 102 with a docking station, by mating the handheld medical scanning device 102 with a power cord plugged into an electrical outlet, etc. In some cases, the handheld medical scanning device 102 may be powered by a power cord plugged into an electrical outlet. The power cord may be used, for example, when the batteries are dead or absent, in order to preserve battery life, etc. The power cord may also be used in instances in which the handheld medical scanning device 102 is not configured to support battery power.

The handheld medical scanning device 102 may be operable to obtain data, e.g., ultrasound data, representative of a patient's anatomy via the imaging element 110. In that regard, the handheld medical scanning device 102 may be operable to image the patient's anatomy via the imaging element. For example, the imaging element 110 may be placed in contact with or in proximity to a patient's skin overlying an area to be imaged. The imaging element 110 may then emit one or more types of energy and receive back energy reflected by the patient's bodily structures. This reflected energy may be used to form images of the patient's anatomy and/or to facilitate assessment of one or more anatomical structures.

As used herein, imaging may refer to the process of scanning with one or more types of energy, e.g., ultrasonic waves, irrespective of whether reflected energy is used to form images. For example, scanning a patient's anatomy with ultrasonic waves in order to obtain data representative of the patient's anatomy, e.g., data which may be used in assessment of an anatomical structure, may be referred to as imaging even if an ultrasound image is not generated based on the obtained data. In that regard, conjugations of "imaging" can be referenced as corresponding conjugations of "scanning," "imaging data" as "scanning data," "imaging preset" as "scanning preset," "imaging procedure" as "scanning procedure," "imaging modality" as "scanning modality," "image collection" as "data collection," "imaging angle" as "scanning angle," "imaging depth" as "scanning depth," "imaging target" as "scanning target," "imaging plane" as "scanning plane," "imaging location" as "scanning location," etc.

The imaging element 110 may comprise an infrared scanner, an ultrasound assembly, e.g., an ultrasound scanner, an optical imaging element, an Optical Coherence Tomography (OCT) scanner, a Computed Tomography (CT) scanner, an X-Ray scanner, or combinations thereof. Accordingly, the handheld medical scanning device 102 may obtain any combination of thermal images, ultrasound images, which may comprise three dimensional (3D) ultrasound images, optical images, OCT images, CT images, and X-ray images. In particular, when the imaging element 110 comprises an ultrasound scanner, the imaging element 110 may comprise one or more ultrasound transducers configured to emit ultrasonic waves into the bodily tissues of the patient. In some cases, ultrasound transducers may be referenced as acoustic elements. The ultrasonic waves may be partially reflected by discontinuities arising from tissue structures, red blood cells, and other features within the patient. Echoes from the reflected ultrasonic waves may be received by the acoustic elements and processed by the handheld medical scanning device 102 to produce an ultrasonic image. In that regard, the handheld medical scanning device 102 can be referenced as an ultrasound imaging device. In some cases, echoes from the reflected ultrasonic waves may be received by the acoustic elements and processed by the handheld medical scanning device 102 to facilitate an assessment of an anatomical structure without an ultrasonic image being produced. In that regard, the handheld medical scanning device 102 can be referenced as an ultrasound scanning device, and the imaging element 110 may be referenced as an ultrasound transducer array or simply as an array.

The imaging element 110 can include one or more acoustic elements. For example, a plurality of acoustic elements can be arranged in an array, e.g., an ultrasound transducer array. For example, an ultrasound transducer array can include any suitable number of individual acoustic elements between 2 acoustic elements and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. The ultrasound transducer array can be any suitable configuration, such as phased array including a planar array, a curved array, etc. For example, the ultrasound transducer array can be a one-dimensional array, 1.x-dimensional array, such as a 1.5-dimensional array, or a two-dimensional array, in some instances. In that regard, the ultrasound transducer or ultrasound transducer array can be configured obtain one-dimensional, two-dimensional, and/or three-dimensional images of the anatomy of the patient. The ultrasound transducer array can be a matrix array, including one or more segments of ultrasound elements (e.g., one or more rows, one or more columns, and/or one or more orientations) that can be uniformly or independently controlled and activated. The imaging element 110 can include any suitable transducer type, including a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof.

In some cases, the imaging element 110 may comprise a miniaturized ultrasound assembly. The miniaturized ultrasound assembly may consume less power, generate less heat, and take up less space within the handheld medical scanning device 102 than would larger ultrasound assemblies. This conservation of space and resources and reduction of heat advantageously permits image processing hardware to be housed within the handheld medical scanning device 102 such that image processing may be performed independently by the handheld medical scanning device 102.

The miniaturized ultrasound assembly may comprise a micro-beamformer. The micro-beamformer may comprise an application-specific integrated circuit (ASIC) that is constructed to accept direct physical connection of individual acoustic elements to the ASIC. The connections may, for example, be made through a ball grid array pin field on a printed circuit board, or directly to the surface of the ASIC itself. For each of the individual acoustic elements there may be time delay circuits within the ASIC that sequence both transmit and receive signals. A proportion of the receive signals may be combined such that the outputs from the micro-beamformer are partially focused analog signals that can be transmitted over a number of signal lines. Combination of the receive signals may advantageously permit the number of signal lines to be substantially reduced from the total acoustic element count. The signals to and from an individual acoustic element may be sequenced with respect to time and position of the individual acoustic element within an overall transducer array. In addition to sequencing of transmit and receive functions the micro-beamformer may also serve to sum receive signals. This method of signal handling enables an entire transducer array to be addressed (via the beam forming circuitry) by a much smaller number of control lines that ultimately connect to the main beamforming signal path. The summation of signals may result in groups of acoustic elements acting as a single transducer. Put differently, the summation of signals may result in groups of small acoustic elements acting as a single large acoustic element. This effective single transducer or patch may comprise acoustic data that is already partially beamformed. The number of patches may have a direct impact on the number of signal lines that connect to the main beamforming signal path. The micro-beamformer may also perform other functions such as generation of a transmit pulse and gain control. In some cases, time delay controls may be used to steer and/or focus a beam formed by the micro-beamformer. The extent to which a beam can be focused or steered may be a function of the total number of acoustic elements on either of the orthogonal axes of a transducer array. The following aspects of a transducer array may promote effective beam forming: small individual acoustic elements, which may permit the acoustic elements to receive and transmit ultrasound waves in multiple directions, where smaller acoustic elements afford larger acceptance angles; maximization of array aperture, which may facilitate focusing; and acoustic elements positioned close together, which may reduce grating lobe artifacts.

A user of the handheld medical scanning device 102 may input instructions to control the operation of the handheld medical scanning device 102 via one or more buttons and/or via the display 112. In that regard, the display 112 may comprise a capacitive or resistive touch screen and may serve as a graphical user interface (GUI). A user may issue touch-based instructions on the display 112 to switch between various screens and a home screen, in order to zoom in on one or more regions of an image, e.g., an ultrasound image, which may comprise a 3D ultrasound image, in order to enter one or more preferences, e.g., a brightness preference, in order to input patient information such as a patient's age, weight, sex, medical condition, etc., in order to access medical data, in order to activate or deactivate scanning with the imaging element 110, in order to select an imaging preset, or combinations thereof.

Prior to imaging with the imaging element 110, a user may select one or more imaging presets. The processor of the handheld medical device is operable to retrieve the imaging presents from a medical database located within the medical facility or a separate server. The database can be represented by a remote medical processing system such as a hospital records system. Alternately, the imaging presents (in shape of a reduced medical database, for example) may be stored in a memory unit disposed within the housing of the device. Selecting an imaging preset may comprise selecting an anatomical structure to be imaged, e.g., a patient's brain, heart, lungs, stomach, spleen, intestines, bladder, kidneys, bones, teeth, liver, uterus, a tumor within the patient, growths within the patient; etc.; selecting a region to be imaged, e.g., a patient's head, neck, chest, abdomen, groin, upper limbs, lower limbs, extremities, etc., or sections thereof such as a quadrant of a patient's abdomen; selecting some other target to be imaged; selecting an imaging depth; selecting an assessment to be performed, e.g., diagnostic assessment, a length measurement, a width measurement, a thickness or depth measurement, an area measurement, a volume measurement, a heart rate measurement, an efficiency measurement, a flow measurement, an ejection fraction measurement, a density measurement, a measurement of change over time, a weight measurement; an angle measurement; etc.; selecting an imaging modality, e.g., thermal imaging, ultrasound, optical imaging, OCT, CT, X-ray, etc.; selecting an imaging angle; selecting desired view; or any combination thereof.

The combination of selected imaging presets may be referenced as a selected imaging procedure. For example, a user may select an imaging procedure for bladder volume measurement by selecting imaging presets identifying a patient's bladder as an anatomical structure to be imaged and volume measurement as an assessment to be performed. For further example, a user may select an imaging procedure for imaging the left ventricular short axis (SAX) of the heart by selecting imaging presets identifying a patient's heart as an anatomical structure to be imaged and the left ventricular short axis as a desired view. In the event that a user does not select any imaging presets, the user has effectively selected general imaging as the imaging procedure.

Imaging presets may be presented for selection on the display 112. A user may make a selection by touching a location on the display 112 occupied by and/or proximate to the desired selection. Imaging presets may appear in a partial or comprehensive list and/or may be separated into categories, e.g., imaging targets, assessments, etc. When imaging presets are separated into categories, a partial or comprehensive list of categories may be displayed, and selection of a category may open a drop down list of imaging presets. Imaging presets selected more frequently may be made more conspicuous than those selected less frequently. For example, frequently selected imaging presets may be highlighted, bolded, pre-selected, displayed first, displayed last, displayed in the center, or any combination thereof. In some cases, a user may choose how the imaging presets appear by altering one or more settings on the handheld medical scanning device 102.

Imaging presets may be presented pre-grouped into imaging procedures, which may similarly be divided into categories as described above. Such pre-grouping of imaging presets may be performed automatically by the handheld medical scanning device 102 and/or may be performed by a user. In that regard, the handheld medical scanning device 102 may be pre-programmed with a list of one or more imaging procedures, may store past imaging procedure selections in a memory for future presentation, may suggest an imaging procedure or modified imaging procedure based past imaging procedure selections and/or patient medical data, may receive a list of one or more imaging procedures from a remote medical processing system, or any combination thereof. As similarly described above, imaging procedures selected more frequently may be made more conspicuous than those selected less frequently.

A user may begin imaging following selection of an imaging procedure. In some cases, the handheld medical scanning device 102 may begin imaging automatically in response to selection of an imaging procedure. In other cases, a user may manually activate imaging independent of selection of an imaging procedure. Once imaging has begun, the handheld medical scanning device 102 may receive imaging data, e.g., ultrasound imaging data, via the imaging element 110.

The handheld medical scanning device 102 may analyze the received imaging data to determine whether or not the received imaging data is relevant to the selected imaging procedure. Imaging data may be relevant to the selected imaging procedure if the imaging data includes imaging data relevant to one or more of the imaging presets defining the selected imaging procedure. In some cases, the received imaging data may only be considered relevant to the selected imaging procedure if it is relevant to each of the imaging presets defining the selected imaging procedure or to a particular imaging preset regardless of its relevance to other imaging presets. Imaging data may be relevant if it includes imaging data representative of an selected imaging target, e.g., an anatomical structure, region, or sub-region; if it includes imaging data at a selected imaging depth; if it includes imaging data useful in performing a selected assessment, e.g., imaging data from which a diagnosis may be made or a measurement taken; if it includes imaging data from a selected imaging angle; if it includes imaging data of a desired view; if it includes imaging data from a selected imaging modality; etc. When general imaging is the selected imaging procedure, e.g., if no imaging presets have been selected, then all imaging data may be considered relevant. Imaging data that is not relevant to a selected imaging procedure may be considered irrelevant and may include, e.g., imaging data representative of air, empty space, or inanimate objects outside a patient's body.

The handheld medical scanning device 102 may filter the received imaging data to segregate relevant imaging data from irrelevant imaging data. The handheld medical scanning device 102 may implement heuristics, e.g., heuristic detection of tissue boundaries, and/or an inference engine employing machine learning techniques in filtering the received imaging data. The inference engine may run on a field-programmable gate array (FGPA) of the handheld medical scanning device 102. Machine learning coefficients for the inference engine may be computed locally and/or remotely and may be stored in a local and/or remote memory, e.g., a flash memory, accessible to the FGPA. Implementation of heuristics and machine learning is described in greater detail in, for example, U.S. Provisional Patent Application No. 62/621,175 filed Jan. 24, 2018, U.S. Provisional Patent Application No. 62/641,493 filed Mar. 12, 2018, U.S. Provisional Patent Application No. 62/641,508 filed Mar. 12, 2018, U.S. Provisional Patent Application No. 62/641,540 filed Mar. 12, 2018, U.S. Provisional Patent Application No. 62/477,536 filed Mar. 28, 2017, and International Patent Application No. PCT/EP2018/058030, all of which are hereby incorporated by reference in their entirety.

The handheld medical scanning device 102 may discard imaging data that is irrelevant to the selected imaging procedure without storing said irrelevant imaging data in a non-volatile memory, e.g., a read only memory (ROM), of the handheld medical scanning device 102. The handheld medical scanning device 102 may discard imaging data irrelevant to a selected imaging procedure by default; however, a user may adjust the settings of the handheld medical scanning device 102 such that imaging data irrelevant to the selected imaging procedure will be retained and stored in a non-volatile memory of the handheld medical scanning device 102. Such setting adjustments may apply to one or more imaging procedures identified by the user or may apply generally to all imaging procedures.

Imaging data irrelevant to the selected imaging procedure may sometimes be temporarily stored in a volatile memory, e.g., a random access memory (RAM), of the handheld medical scanning device 102, which may allow a user to review imaging data classified as irrelevant prior to its being discarded by the handheld medical scanning device 102. In that regard, a user may optionally instruct that imaging data which would ordinarily be discarded be instead stored in non-volatile memory, e.g., local and/or remote non-volatile memory.

In some cases, imaging data irrelevant to a selected imaging procedure may be discarded without any further processing, e.g., without an image being generated based on said irrelevant imaging data. In other cases, an image may be generated based on such irrelevant imaging data and may be outputted to the display 112 for review prior to being discarded. Upon reviewing the displayed image, a user may optionally instruct that the irrelevant imaging data from which the image was generated be stored in non-volatile memory, e.g., local and/or remote non-volatile memory, rather than discarded.

The handheld medical scanning device 102 may track one or more device metrics such as battery life and may modify its behavior based on current metrics. For example, in order to preserve battery life, the handheld medical scanning device 102 may discard irrelevant imaging data without first generating and displaying an image based on the irrelevant imaging data when the handheld medical scanning device 102 is low on battery even if the handheld medical scanning device 102 would ordinarily display the image prior to discarding the irrelevant imaging data. Battery life may be low when it falls below 50%, below 40%, below 30%, below 25%, below 20%, below 15%, below 10%, below 5%, within 5% of an average amount expended for a selected imaging procedure, within 5% of an average amount expended during a single use, or combinations thereof.

The handheld medical scanning device 102 may select one or more imaging planes across which to scan a patient's anatomy. The one or more imaging planes may be selected based on the condition that a scan across said imaging planes generates imaging data relevant to the selected imaging procedure, e.g., imaging data of an anatomical structure to be imaged. Once the one or more imaging planes have been selected, the handheld medical scanning device 102 may scan the patient's anatomy across only the selected imaging planes. For example, the device 102 may first conduct an initial ultrasound scan to determine the relevant imaging planes and/or identify a region/anatomy of interest within a volume. For example, the initial scan can be a sparse scan in that relatively less ultrasound data is obtained (e.g., only enough ultrasound data to determine the relevant imaging planes and/or identify the region/anatomy of interest). After the relevant imaging planes are determined and/or the region/anatomy of interest is identified, the device 102 conducts a further scan during which ultrasound beams are focused towards the relevant imaging planes for real-time acquisition for imaging or data-gathering. The second scan can obtain relatively more ultrasound data than the initial, sparse scan because the relevant anatomy/region of interest has already been identified. Accordingly, the device 102 obtains enhanced, high quality data at the relevant images planes while advantageously avoiding obtaining irrelevant data. Scanning across only the selected imaging planes may advantageously reduce the acquisition of irrelevant imaging data, may reduce power consumption and preserve battery life, and may improve the quality of the imaging data acquired.

The handheld medical scanning device 102 may store imaging data relevant to the imaging presets and/or the selected imaging procedure in a non-volatile memory of the handheld medical scanning device 102. Imaging data stored in local non-volatile local memory may remain available for review, analysis, transmission, etc., even after the handheld medical scanning device 102 has been power cycled. Storage in local non-volatile memory may provide several advantages, including the ability to delay a transmission to a remote medical processing system until such time as a link, e.g., a wireless connection or a wired connection, is available. In the event that imaging data stored in a non-volatile memory of the handheld medical scanning device 102 is transmitted to a remote non-volatile memory, e.g., that of a remote medical processing system such as a hospital records system, the handheld medical scanning device 102 may delete said imaging data from its local non-volatile memory. In some cases, the handheld medical scanning device 102 may delete imaging data stored in its local non-volatile memory after a set amount of time, which may be predetermined by the manufacturer or chosen by a user.

Imaging data may be stored in an imaging data file. Storing only relevant imaging data may advantageously reduce the size of imaging data files, which may conserve memory space and may enable the handheld medical scanning device 102 to store more imaging data files than it could otherwise. Smaller imaging data files may also be transmitted to a remote medical processing system, e.g., a hospital system, more quickly, more reliably, and may consume less bandwidth when transmitted. Imaging data files containing only relevant imaging data may also provide for more efficient processing, e.g., in performance of an anatomical assessment, given that irrelevant input has been pre-filtered thereby reducing the processing burden.

Imaging data relevant to a selected imaging procedure may be processed in order to generate an image, e.g., an ultrasound image, which may comprise a 3D ultrasound image, for display on the display 112. Imaging data relevant to a selected imaging procedure may be analyzed to generate an assessment result such as a diagnosis or measurement. The analysis may be performed by one or more of the handheld medical scanning device 102, by a user of the handheld medical scanning device 102, by a remote medical processing system, or by a user of the remote medical processing system. The assessment result may be stored in a non-volatile memory of the handheld medical scanning device 102 and/or in a remote non-volatile memory and may be displayed on the display 112. Assessment results may be displayed concurrently with images, e.g., ultrasound images, which may comprise 3D ultrasound images, associated with the imaging data from which the assessment results were derived. In that regard, the handheld medical scanning device 102 may highlight areas of interest within the images, may display measurements of anatomical structures within the images, may superimpose assessment results over images to which they relate, or may perform combinations thereof.

In some cases, the handheld medical scanning device 102 may be unable to classify received imaging data. This may occur if the handheld medical scanning device 102 experiences a shortage of processing resources or if handheld medical scanning device 102 is unsure how to interpret the received imaging data. Unclassified imaging data may be treated as irrelevant or may be treated as relevant. Treatment of unclassified imaging data may be determined at least in part on one or more of a selected user preference, a selected imaging procedure, on one or more device metrics, e.g., available storage space in a local non-volatile memory, available processing resources, etc.

The handheld medical scanning device 102 may provide guidance to a user during imaging. Such guidance may be provided in real time, e.g., as the handheld medical scanning device is obtaining imaging data. In that regard, the handheld medical scanning device 102 may output one or more indications to aid a user in positioning the handheld medical scanning device 102 at a suitable imaging location. A suitable imaging location may be determined based on a selected imaging procedure and/or selected imaging presets defining an imaging procedure. For example, when a patient's heart is selected as an anatomical structure to be imaged, a suitable imaging location may be one at which the handheld medical scanning device 102 can obtain imaging data representative of the patient's heart. In some cases, e.g., when multiple imaging presets have been selected, the ability of the handheld medical scanning device 102 to obtain imaging data representative of a selected anatomical structure may not be sufficient to qualify an imaging location as a suitable imaging location. For example, when a patient's bladder is selected as an anatomical structure to be imaged and a volume measurement is selected as an assessment to be performed, a suitable imaging location may be one at the handheld medical scanning device 102 can obtain imaging data that is both representative of the patient's bladder and useable to calculate the volume of the patient's bladder.

The handheld medical scanning device 102 may analyze received imaging data to determine whether or not the handheld medical scanning device 102 is positioned at a suitable imaging location, e.g., by determining whether the received imaging data included imaging data representative of a selected anatomical structure to be imaged. If the handheld medical scanning device 102 determines that it is not positioned at a suitable imaging location, the handheld medical scanning device 102 may output an indication to alert a user to reposition the handheld medical scanning device 102. The indication may comprise one or more of a visual indication, e.g., a picture, an arrow, text, a color, a sign, a symbol, an "X," a light, etc., which may in some cases be displayed on the display 112; an audible indication, e.g., a tone, a chime, a beep, a buzz, a ring, a frequency, etc.; or a tactile indication, e.g., a buzz, a vibration, an electrical pulse, etc.

The indication to alert a user to reposition the handheld medical scanning device 102 may comprise a suggested positioning adjustment. In that regard, the handheld medical scanning device 102 may analyze received imaging data and determine a positioning adjustment to suggest based on the received imaging data in view of a selected imaging procedure and/or selected imaging presets defining an imaging procedure. Indications comprising suggested adjustments may convey information about the magnitude of the suggested adjustment. For example, such indications may include one or more of numerical measurements, e.g., 1 cm, 2 cm, etc.; color coding, e.g., red to suggest that the user is "hot," i.e., very close to reaching a suitable imaging position and should make only small adjustments, or blue to suggest that the user is "cold," i.e., far from reaching a suitable imaging position and should make larger adjustments, etc.; such indications may be variable in size, e.g., a large arrow may suggest a large adjustment while a small arrow suggests a small adjustment; etc.

Determining the position adjustment suggestion may comprise determining the presence and/or absence of imaging data representative of one or more anatomical structures in the received imaging data. For example, the handheld medical scanning device 102 may determine that a portion of a patient's heart is in view toward one side of the handheld medical scanning device 102. In order to bring the full heart into view, e.g., when the patient's heart is selected as an anatomical structure to be imaged, the handheld medical scanning device 102 may output an indication, e.g., an arrow or textual instruction, suggesting that the handheld medical scanning device 102 be moved toward that side.

The handheld medical scanning device 102 may be programmed with and/or may learn information about anatomy, e.g., human and/or animal anatomy and may store such information in memory such as non-volatile memory. In that regard, the handheld medical scanning device 102 may be able to determine its location based on received imaging data and stored anatomical information. For example, the handheld medical scanning device 102 may determine that a patient's stomach is in view toward a first side of the handheld medical scanning device 102 while the patient's large intestine is in view toward a second side of the handheld medical scanning device 102. In order to bring the patient's bladder into view, e.g., when the patient's bladder is selected as an anatomical structure to be imaged, the handheld medical scanning device 102 may determine, e.g., by consulting stored anatomical information, that the handheld medical scanning device 102 should be moved toward the second side and may output an indication suggesting that the handheld medical scanning device 102 be moved toward the second side.

In some cases, the handheld medical scanning device 102 may automatically adjust the angle of a scan based on the location of the handheld medical scanning device 102 relative to, e.g., an anatomical structure to be imaged. For example, the handheld medical scanning device 102 may adjust the emission of ultrasonic waves such that a scanning angle is adjusted. Such adjustments may be made while the handheld medical scanning device 102 is stationary. This may advantageously expand the area which may be considered a suitable imaging location and may reduce the amount of manual adjustment performed by users thereby reducing frustration. Automatic adjustment of the angle of a scan may be based on irrelevant imaging data, e.g., imaging data that does not include an anatomical structure to be imaged, and may facilitate acquisition of relevant imaging data, e.g., imaging data that includes an anatomical structure to be imaged. For example, automatic adjustment of the angle of a scan may bring into view an anatomical structure to be imaged.

Once the handheld medical scanning device 102 determines that it has reached a suitable imaging location, it may output an indication to that effect. The indication may alert the user to maintain the current position of the handheld medical scanning device. The indication may comprise one or more of a visual indication, e.g., a picture, an arrow, text, a color, a sign, a symbol, an "X," a light, etc., which may in some cases be displayed on the display 112; an audible indication, e.g., a tone, a chime, a beep, a buzz, a ring, a frequency, etc.; or a tactile indication, e.g., a buzz, a vibration, an electrical pulse, etc. The handheld medical scanning device 102 may be manually held at the suitable imaging location or may be attached to a patient's body at the suitable imaging location, e.g., via suction, adhesive, magnetism, elastics, a strap, cohesion, via some other technique, or via combinations thereof.

The handheld medical scanning device 102 may also output an indication when image collection has finished, which may alert a user that the handheld medical scanning device 102 may be moved from the suitable imaging position, e.g., removed from contact with a patient's body. Image collection may automatically finish in response to the handheld medical scanning device 102 determining, e.g., by analyzing received imaging data, that sufficient imaging data has been collected to perform a selected assessment, that a selected view has been obtained, that a selected imaging angle has been achieved, that a selected depth has been imaged, that a selected anatomical structure has been imaged, or any combination thereof. Image collection may finish at different times and/or in response to different determinations depending on the selected imaging procedure and/or imaging presets defining the selected imaging procedure. For example, when a patient's bladder is selected as an anatomical structure to be imaged and a volume measurement is selected as an assessment to be performed, imaging may automatically finish in response to determining that sufficient imaging data has been collected to determine the volume of the patient's bladder based on the collected imaging data. For further example, imaging may continue until manually deactivated when general imaging is selected as the imaging procedure, e.g., when no imaging presets are selected.

When a selected imaging procedure includes selection of an assessment to be performed, received imaging data may be analyzed in real time to generate an assessment result. As used herein, analyzing imaging data in real time may comprise analyzing imaging data contemporaneously with reception, instantly upon reception, within a fraction of a second of reception, within a time period of reception imperceptible to an unaided human, within 1 second of reception, within two seconds of reception, within three seconds of reception, within five seconds of reception, or analyzing imaging data received as part of an imaging procedure while that imaging procedure remains ongoing. In some cases, the handheld medical scanning device 102 may determine an assessment result by the time imaging is finished. Determination of the assessment result may trigger the handheld medical scanning device 102 to finish imaging. In that regard, imaging may finish contemporaneously with determination of the assessment result, instantly upon determination of the assessment result, within a fraction of a second of determination of the assessment result, within a time period of determination of the assessment result imperceptible to an unaided human, within 1 second of determination of the assessment result, within two seconds of determination of the assessment result, within three seconds of determination of the assessment result, within five seconds of determination of the assessment result, or within some other timeframe of determination of the assessment result.

When there is a wait time between when imaging is finished and determination of an assessment result, the handheld medical scanning device 102 may output an indication alerting a user that imaging data is being processed. The indication may comprise one or more of a visual indication, e.g., a picture, an arrow, text, a color, a sign, a symbol, an "X," a light, etc., which may in some cases be displayed on the display 112; an audible indication, e.g., a tone, a chime, a beep, a buzz, a ring, a frequency, etc.; or a tactile indication, e.g., a buzz, a vibration, an electrical pulse, etc. For example, the indication may comprise an hour glass, a revolving icon, text, or combinations thereof. Wait times may occur when, e.g., determination of an assessment result is made by a remote medical processing system rather than the handheld medical scanning device 102.

The various indications described above may provide guidance to a user during imaging and may advantageously increase the likelihood that useful imaging data will be obtained and reduce the likelihood of user error, e.g., removing the handheld medical scanning device 102 before imaging is completed. Such guidance may be particularly useful to inexperienced users. Users may have the option to adjust the settings of the handheld medical scanning device 102 such that one or more of the indications is deactivated. The ability to deactivate indications may be beneficial for experienced users who may be comfortable working without the guidance provided by the indications.

The handheld medical scanning device 102 may output images, e.g., ultrasound images, which may comprise 3D ultrasound images, generated based on imaging data received from the imaging element 110 to the display 112. Such images may be outputted to the display 112 during imaging and/or after imaging has finished. In some cases, only images generated from imaging data relevant to a selected imaging procedure may be outputted to the display 112. This may advantageously prevent a user from wasting their time reviewing irrelevant images, e.g., images generated based on imaging data irrelevant to a selected imaging procedure. In some cases, only images generated from imaging data received during a particular portion of an imaging session may be outputted to the display 112. For example, the handheld medical scanning device 102 may only output images to the display 112 that are generated based on imaging data received after the handheld medical scanning device 102 is positioned at a suitable imaging location.

In some cases, the handheld medical scanning device 102 may not output anatomical images, e.g., ultrasound images, which may include 3D ultrasound images, at all. Instead, the handheld medical scanning device 102 may output one or more indications, e.g., one or more of the indications described above, during imaging and may output one or more assessment results once sufficient imaging data has been obtained. Whether the handheld medical scanning device 102 outputs anatomical images to the display 112 may be determined by default programming of the handheld medical scanning device 102 and/or by setting preferences chosen by a user.

Images of anatomical structures may be difficult for a non-medically trained user, such as a patient, to understand. Such users may find it easier to comprehend medical information presented in the form of assessment results, e.g., measurements and diagnoses, than to comprehend anatomical images. Accordingly, outputting an assessment result without outputting anatomical images may advantageously reduce the likelihood that a non-medically trained user will become frustrated while using the handheld medical scanning device and increases the likelihood that such a user will understand the medical information displayed.

Figure 2:
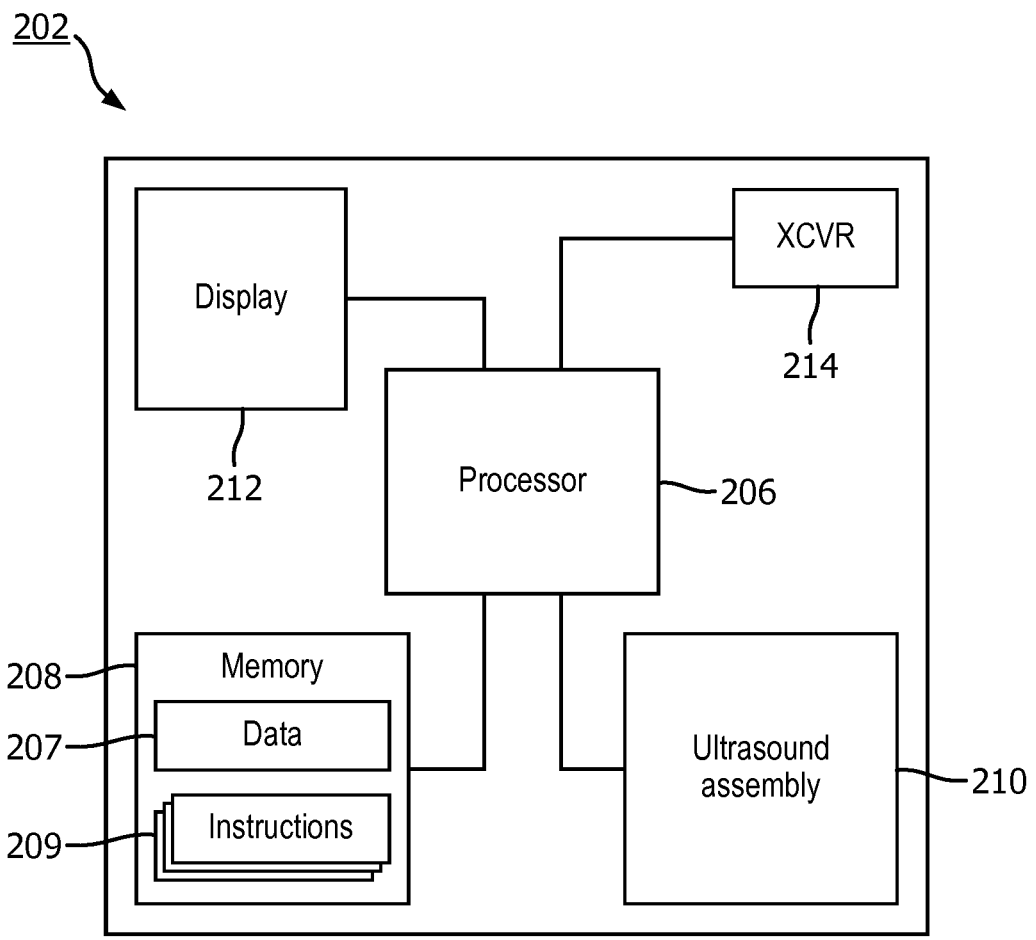
FIG. 2 is a diagrammatic schematic view of a handheld medical scanning device, according to aspects of the present disclosure.

Turning now to FIG. 2, shown therein is a diagrammatic schematic view of a handheld medical scanning device 202, according to aspects of the present disclosure. The handheld medical scanning device 202 may include a memory 208 with data 207 and a plurality of instructions 209 stored therein, an ultrasound assembly 210, a display 212, and a radiofrequency transceiver 214 each in communication with a processor 206.

The memory 208 may comprise a non-volatile memory and/or a volatile memory. The data 207 may comprise any type of data including medical data such as: imaging data, e.g., imaging data files, assessment results, diagnoses, measurements, treatment plans, medication schedules, test results, appointment schedules, progress reports, a patient history, etc. The plurality of instructions 209 may comprise instructions which, when executed by the processor 206, cause the processor to perform one or more of the techniques described herein. For example, the plurality of instructions 209 may comprise one or more of heuristic algorithms, machine learning algorithms, device positioning algorithms, algorithms for processing imaging data, algorithms for segregating relevant imaging data from irrelevant imaging data, etc.

The processor 206 may operate the ultrasound assembly 210, which may be miniaturized, and which may comprise an ultrasound transducer array in some instances, to obtain imaging data and may receive such imaging data from the ultrasound assembly 210. The processor 206 may generate images based on the received imaging data and may output such images, e.g., ultrasound images, which may comprise 3D ultrasound images, to the display 212. The processor 206 may also receive user input via the display 212. For example, the processor 206 may retrieve a selection of the imaging presets and receive the selected imaging preset in response to a user input via the display 212. The processor 206 may operate the radiofrequency transceiver 214 to communicate with the remote medical processing system, e.g., a hospital record system or other hospital system. Alternatively, the communication between the processor and the remote medical processing system may be realized via a wired communication. The radiofrequency transceiver 214 may be configured to communicate over an Institute of Electrical and Electronics Engineers (IEEE) 802.11 (WiFi) link, a Bluetooth link, a Zigbee link, an ultra-wideband (UWB) link, or over any combination thereof. In some cases, the handheld medical scanning device 202 may comprise multiple radiofrequency transceivers 214, and different radiofrequency transceivers 214 may be configured to communicate over different links. In that regard, different radiofrequency transceivers 214 may be configured to communicate over different frequencies, different time slots, etc.

Figure 3:
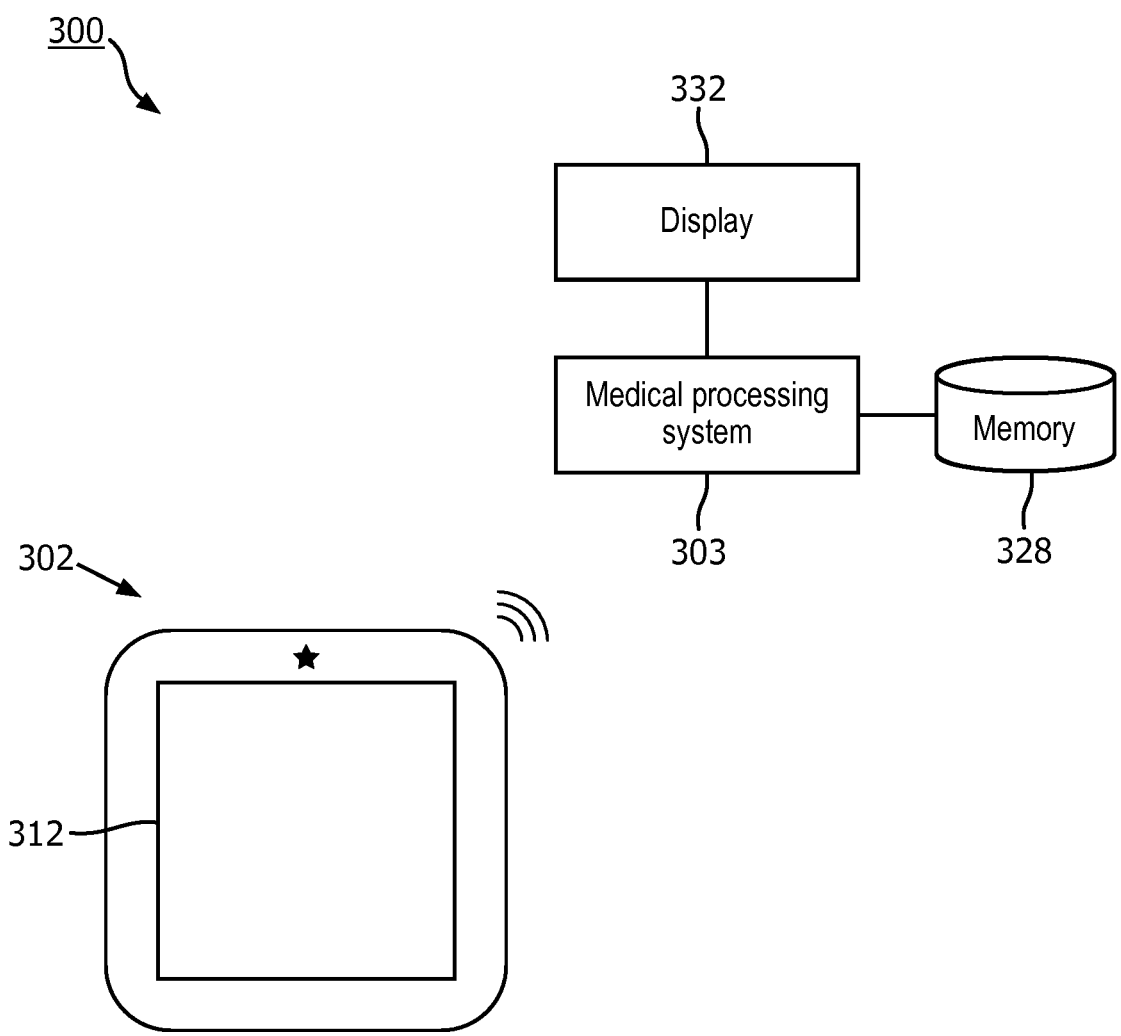
FIG. 3 is a diagrammatic schematic view of a distributed medical processing system, according to aspects of the present disclosure.

Turning now to FIG. 3, a system 300 is described. The system 300 comprises a handheld medical scanning device 302 and a remote medical processing system 303. The handheld medical scanning device 302 comprises a display 312, and the remote medical processing system 303 is in communication with a display 332 and a memory 328. The display 332 and/or the memory 328 may communicate with the medical processing system 303 over a wired and/or over a wireless link. In some cases, the memory 328 may comprise a picture archiving system (PAC). Though the handheld medical scanning device 302 may optionally communicate with the remote medical processing system 303, the handheld medical scanning device 302 may be configured to operate autonomously. For example, the handheld medical scanning device 302 may analyze imaging data, may provide positioning guidance to a user, may generate and display images, may selectively store and delete imaging data, etc., autonomously without assistance from the remote medical processing system 303.

The handheld medical scanning device 302 may send and receive medical data, e.g., imaging data, one or more aspects of a patient's medical history, assessment results, etc., to the remote medical processing system 303. Such medical data may be sent over a wired and/or over a wireless connection. The remote medical processing system 303 may analyze medical data, e.g., imaging data, received from the handheld medical scanning device 302 and may communicate its findings, e.g., assessment results, back to the handheld medical scanning device 302. In some cases, a user of the remote medical processing system 303 may analyze medical data received from the handheld medical scanning device 302. For example, the remote medical processing system 303 may generate an image based on imaging data received from the handheld medical scanning device 302 and may output said image to the display 332 for review. The user may annotate the displayed images, may write up a diagnosis, may perform measurements on the images, may devise a treatment plan to be followed, or any combination thereof, which may be communicated back to the handheld medical scanning device 302 for review by a user of that device. In some cases, a patient may be a user of the handheld medical scanning device 302. In that regard, the patient may be able to receive medical attention, including diagnoses and treatment recommendations, via the handheld medical scanning device 302 while outside of a hospital setting, e.g., while the patient is at home.

Figure 4:
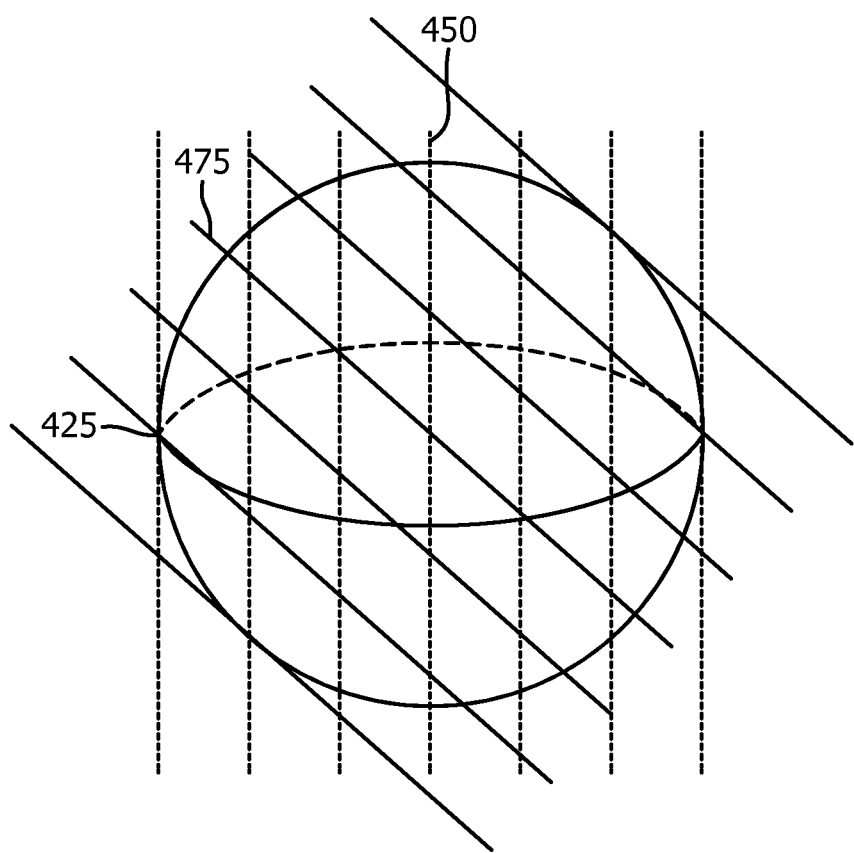
FIG. 4 is a diagrammatic schematic view of an anatomical structure being imaged across a plurality of orthogonal imaging planes, according to aspects of the present disclosure.

Turning now to FIG. 4, shown therein is a tissue volume 425 being scanned across plurality of imaging planes, including imaging planes 450 and 475. Tissue volume 425 may be representative of any anatomical structure within a patient, e.g., a patient's brain, heart, lungs, stomach, spleen, intestines, bladder, kidneys, bones, teeth, liver, uterus, a tumor within the patient, growths within the patient, etc. The tissue volume 425 may be scanned, e.g., by a handheld medical scanning device, across any imaging plane in three dimensional space. For the sake of clarity, only a subset of the set of all possible imaging planes is shown in FIG. 4. The tissue volume 425 may be scanned as part of an imaging procedure, e.g., an ultrasound, including a 3D ultrasound, imaging procedure. As similarly described above, a handheld medical scanning device may analyze imaging data obtained from scanning across multiple imaging planes and may filter the imaging data to segregate relevant imaging data from irrelevant imaging data, may output one or more indications, e.g., indications providing positioning guidance, may generate and output one or more assessment results, etc.

By way of particular example, and without limitation, the tissue volume 425 may comprise a patient's bladder and may scanned with ultrasound as part of an imaging procedure to measure the patient's bladder volume. In that regard, a handheld medical scanning device may be positioned at a suitable imaging location for obtaining ultrasound data to be used in calculating the patient's bladder volume. When the handheld medical scanning device is positioned at the suitable imaging location, an ultrasound assembly of the handheld medical scanning device may scan the patient's bladder across a plurality of imaging planes over a variety of elevation positions and rotations. The handheld medical scanning device may identify two imaging planes which represent orthogonal, or substantially orthogonal, complete views of the patient's bladder, e.g., imaging planes 450 and 475 in FIG. 4. These two imaging planes may provide sufficient imaging data to calculate the volume of the patient's bladder. Accordingly, ultrasound data from imaging planes 450 and 475 may be classified as ultrasound data relevant to the selected imaging procedure. Imaging data from all other imaging planes may be classified as irrelevant to the selected imaging procedure and may be discarded. Bladder volume may be calculated from imaging data obtained from imaging planes 450 and 475 by performing heuristic edge detection on a bladder cavity in each view, calculating the area of the bladder cavity in each view, averaging the calculated bladder cavity area for each view, and rotating the calculated average about its central axis. Ultrasound images of the patient's bladder and/or the bladder volume measurement may be outputted to a display of the handheld medical scanning device.

Also by way of particular example, and without limitation, the tissue volume 425 may comprise a patient's heart and may scanned with ultrasound as part of an imaging procedure to image the patient's heart along the left ventricular short axis. In that regard, a handheld medical scanning device may be positioned at a suitable imaging location for imaging the patient's heart along the left ventricular short axis, e.g., at the patient's left upper chest. When the handheld medical scanning device is positioned at the suitable imaging location, an ultrasound assembly of the handheld medical scanning device may scan the patient's heart across a plurality of imaging planes over a variety of elevation positions and rotations. The handheld medical scanning device may identify an imaging plane which represents a view along the left ventricular short axis, e.g., imaging plane 450 in FIG. 4. Imaging data from imaging plane 450 may be classified as imaging data relevant to the selected imaging procedure. Imaging data from all other imaging planes may be classified as irrelevant to the selected imaging procedure and may be discarded. Once the imaging plane 450 has been identified as providing a view along the left ventricular short axis, the handheld medical scanning device may scan along the imaging plane 450 to obtain a series of images at a full frame rate thereby creating an image loop of one or more heart cycles which may be stored in a non-volatile memory of the handheld medical scanning device. Even with all other views discarded, an image data file of the image loop may consume 2 megabytes (MB) or more per loop—a fact which underscores the utility of the data reduction techniques described herein. Ultrasound images of the patient's heart, e.g., images along the left ventricular short axis, may be outputted to a display of the handheld medical scanning device.

Figure 5C:
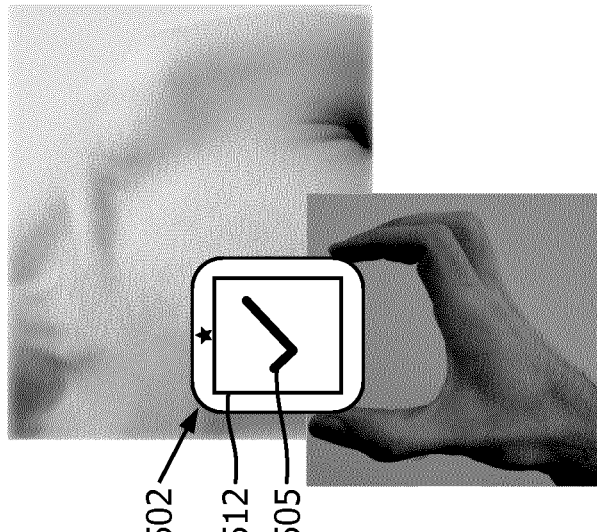
FIG. 5C is a diagrammatic top view of a handheld medical scanning device displaying an indication, according to aspects of the present disclosure.
Figure 5B:
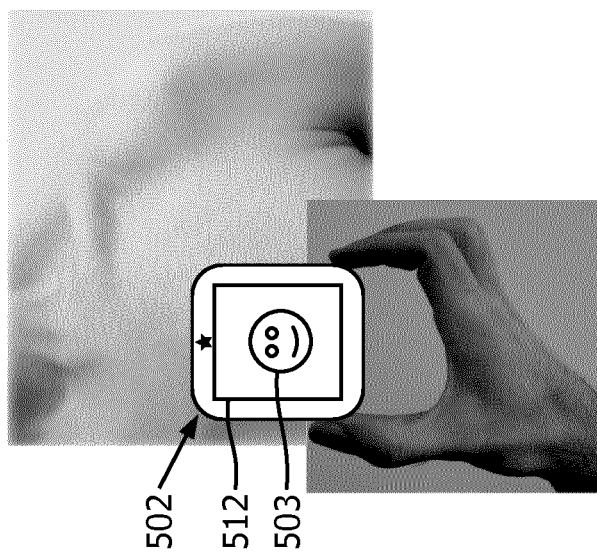
FIG. 5B is a diagrammatic top view of a handheld medical scanning device displaying an indication, according to aspects of the present disclosure.
Figure 5A:
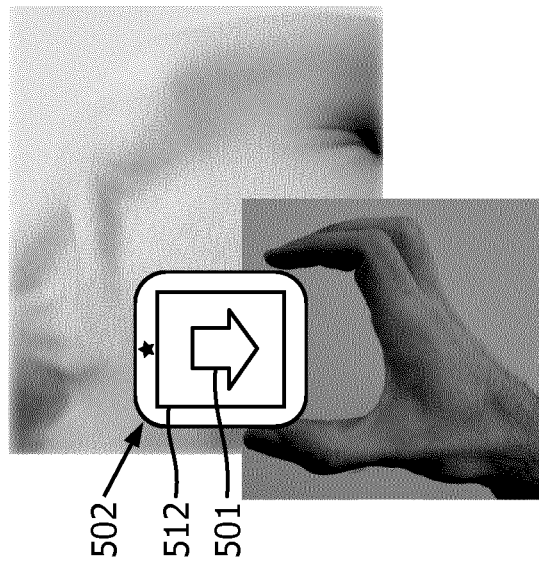
FIG. 5A is a diagrammatic top view of a handheld medical scanning device displaying an indication, according to aspects of the present disclosure.

Turning now to FIGS. 5A-5C, shown therein is a handheld medical scanning device 502 displaying various indications while manually held against or proximate to a patient's body. The display 512 can include a graphical, visual, textual, numerical, and/or otherwise suitable representation, without an ultrasound image in some instances. The handheld medical scanning device 502 is shown as being positioned at or near a patient's left upper chest. The handheld medical scanning device 502 may be positioned in such a location in order to, for example, image a patient's heart along the left ventricular short axis. FIG. 5A depicts the handheld medical scanning device 502 displaying an indication 501 on a display 512. The indication 501 may be displayed in response to the medical scanning device 502 determining that it is not positioned in a suitable imaging location. In that regard, the indication 501 may alert a user to reposition the medical scanning device 502. In some cases, the indication 501 may comprise an adjustment suggestion determined by the medical scanning device 502. For example, the indication 501 illustrated in FIG. 5A comprises an arrow, which may alert the user to reposition the handheld medical scanning device 502 lower on the patient's chest, e.g., to a position shown in FIGS. 5B and 5C. FIG. 5B shows an indication 503 displayed on the display 512. The handheld medical scanning device 502 may output the indication 503 to the display 512 in response to determining that it is positioned at a suitable imaging location. The indication 503 may alert the user not to move the handheld medical scanning device 502 and/or may alert the user that relevant imaging data is being obtained. FIG. 5C shows an indication 505 displayed on the display 512. The handheld medical scanning device 502 may output the indication 505 to the display 512 in response to determining that an imaging procedure has finished, in response to determining that sufficient imaging data has been obtain in order to perform a selected assessment, etc. The indication 505 may alert the user that the handheld medical scanning device 502 can be moved, e.g., removed from the patient's body and/or repositioned to perform another imaging procedure.

Figure 6B:
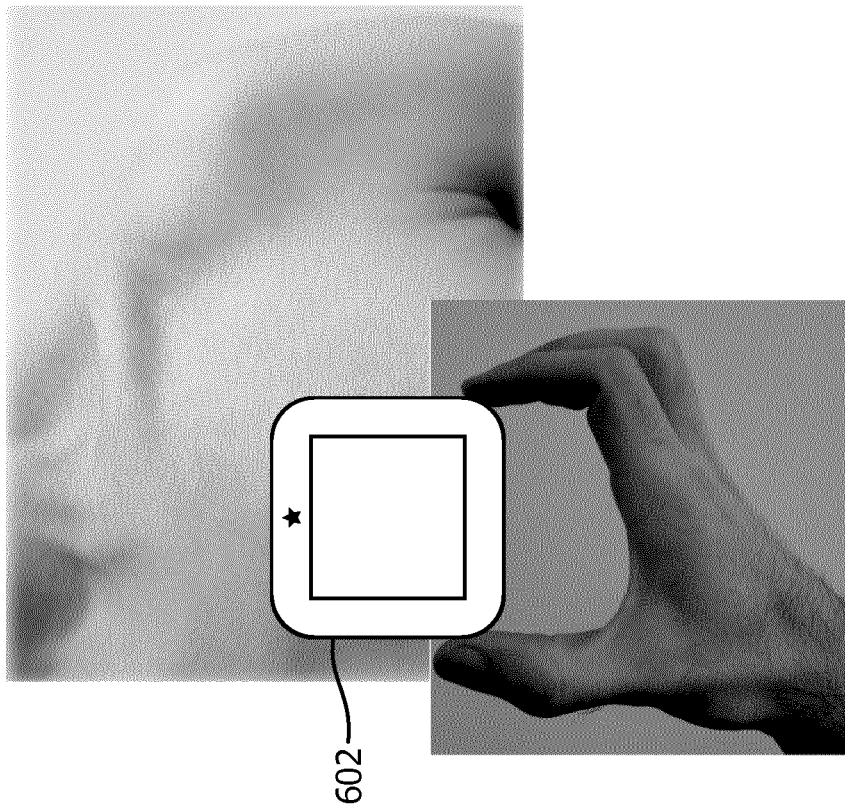
FIG. 6B is a diagrammatic top view of a handheld medical scanning device manually held against a patient's body at a scanning location, according to aspects of the present disclosure.
Figure 6A:
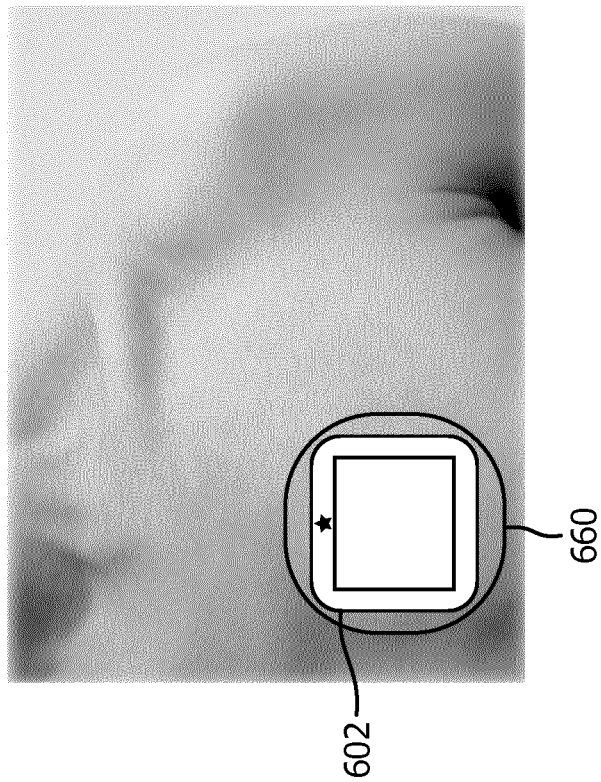
FIG. 6A is a diagrammatic top view of a handheld medical scanning device attached to a patient's body at a scanning location, according to aspects of the present disclosure.

Turning now to FIGS. 6A and 6B, shown therein is a handheld medical scanning device positioned in a suitable imaging location. The handheld medical scanning device 602 is shown as being positioned at or near a patient's left upper chest. The handheld medical scanning device 602 may be positioned in such a location in order to, for example, image a patient's heart along the left ventricular short axis. FIG. 6A shows the handheld medical scanning device 602 adhered to the patient's body at the suitable imaging location with an attachment 660. In that regard, the attachment 660 may comprise an adhesive, e.g. a sticky substance, rosin, stickum, tape, etc.; may be configured to provide suction; may be electromagnetically charged; may comprise an elastic; may comprise a strap; etc. Attachment 660 may be integrated into the handheld medical scanning device 602 or may be removable. FIG. 6B shows the handheld medical scanning device 602 held manually at the suitable imaging location with an attachment 660. A user of the handheld medical scanning device 602 may choose whether to maintain the handheld medical scanning device 602 at a suitable imaging location manually or via the attachment 660.

Figure 7B:
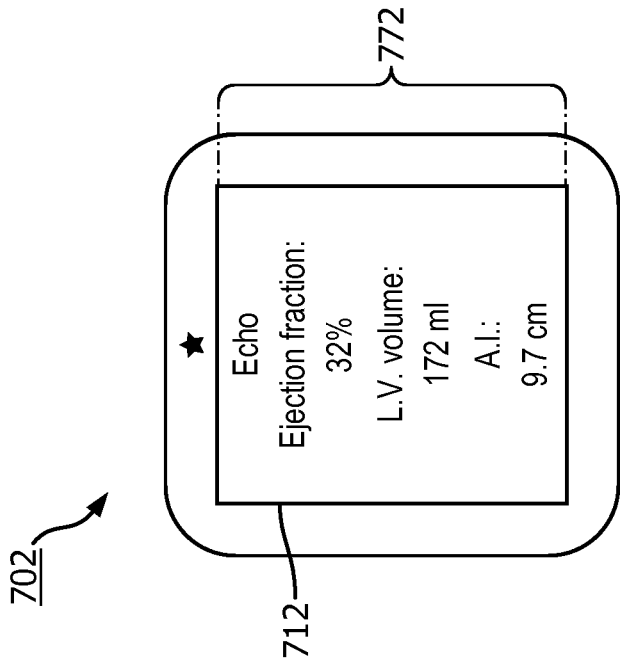
FIG. 7B is a diagrammatic top view of a handheld medical scanning device displaying medical information, according to aspects of the present disclosure.
Figure 7A:
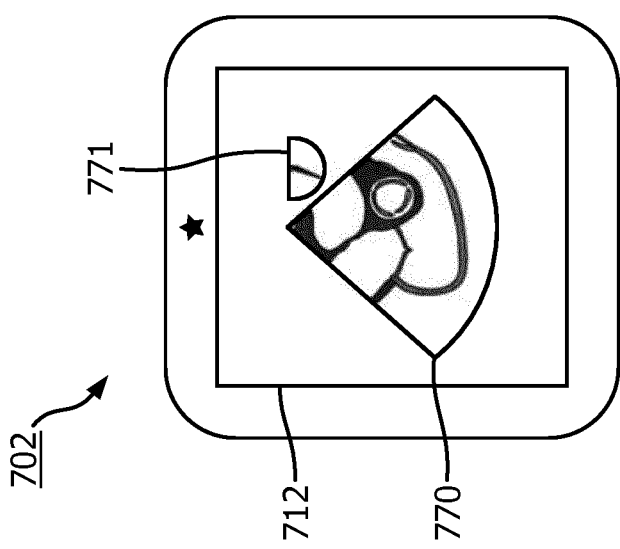
FIG. 7A is a diagrammatic top view of a handheld medical scanning device displaying medical information, according to aspects of the present disclosure.

Turning now to FIGS. 7A and 7B, shown therein is a handheld medical scanning device 702 displaying various types of medical data. In FIG. 7A, an ultrasound image 770 is shown on a display 712 of the handheld medical scanning device 702. Though the ultrasound image 770 may be representative of a view of a patient's heart taken along the left ventricular short axis in FIG. 7A, it should be understood that any ultrasound image may similarly be displayed on the display 712. A gauge 771 may also be displayed on the display 712 either concurrently with or independently of ultrasound image 770. The gauge 771 may provide information about one or more of an imaging angle, an imaging depth, etc. In some cases, anatomical images, e.g., ultrasound image 770, may be difficult for a user, especially a non-medically trained user, to understand. Accordingly, the handheld medical scanning device 702 may additionally or alternatively display assessment results on display 712, as shown in FIG. 7B. The display 712 of FIG. 7B can include a graphical, visual, textual, numerical, and/or otherwise suitable representation, without an ultrasound image in some instances. In that regard, FIG. 7B shows assessment results 772 displayed on the display. As shown in FIG. 7B, the assessment results 772 comprise an ejection fraction, a volume measurement of a patient's left ventricle, and an A.L. measurement, which may, for example, include one of an aortic length, an apical length, an apex location, an axial length, an area-length calculation, an atrial length, an array length, e.g., a length of an array of the imaging element 110 described hereinabove, an anterolateral measurement, e.g., an anterolateral diameter or anterolateral-posteromedial diameter, etc. The assessment results 772 shown in FIG. 7B may have been generated based on imaging data from a view of a patient's heart taken along the left ventricular short axis. Though only a few assessment results are shown in FIG. 7B, it should be understood that any assessment result may be similarly displayed on the display 712.

Figure 8:
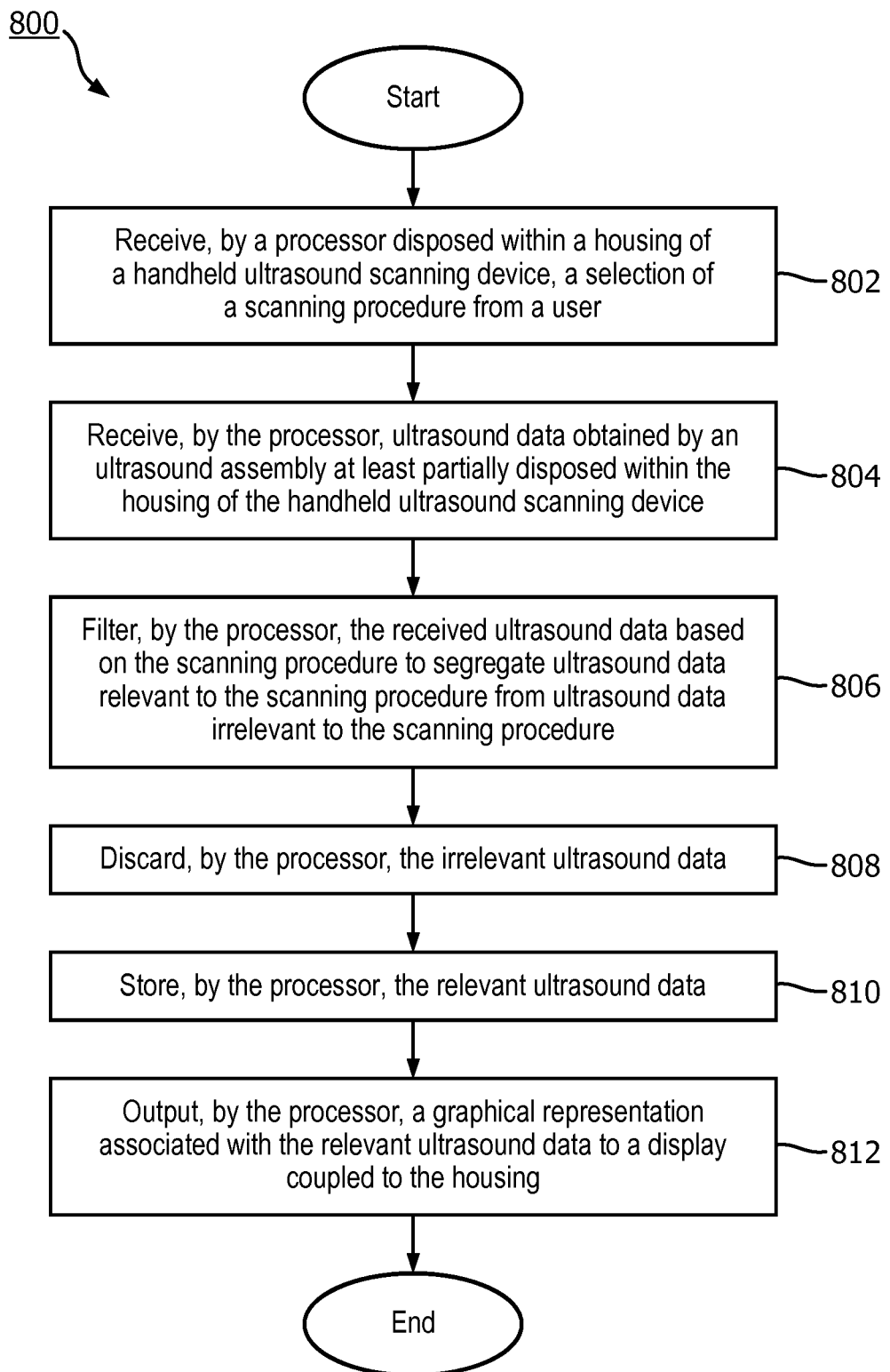
FIG. 8 is a flow chart of a method, according to aspects of the present disclosure.

Turning now to FIG. 8, a method 800 is described. The method 800 may be implemented by or with any of the handheld medical scanning devices described herein, e.g., handheld medical scanning devices 102, 202, 302, 402, 502, 602, and 702. The method begins at step 802 where a selection of a scanning procedure is received from a user by a processor disposed within a housing of a handheld ultrasound scanning device. At step 804, the processor receives ultrasound data obtained by an ultrasound assembly at least partially disposed within the housing of the handheld ultrasound scanning device. The processor filters, at step 806, the received ultrasound data based on the scanning procedure in order to segregate ultrasound data relevant to the scanning procedure from ultrasound data irrelevant to the scanning procedure. At step 808, the processor discards the irrelevant ultrasound data. At step 810, the processor stores the relevant ultrasound data. Storing the relevant ultrasound data may comprise wirelessly communicating the relevant ultrasound data to a remote memory for storage. Storing the relevant ultrasound data may comprise storing the relevant ultrasound data in a local memory of the handheld ultrasound scanning device. The processor outputs a graphical representation associated with the relevant ultrasound data to a display coupled to the housing at step 812. The method may further include generating, by the processor, a graphical representation associated with the relevant ultrasound data. The method may further include generating, by the processor, a graphical representation associated with the irrelevant ultrasound data, and outputting, by the processor, the graphical representation associated with the irrelevant ultrasound data to a display of the handheld ultrasound scanning device prior to discarding the irrelevant ultrasound data. The method may further include analyzing, by the processor, the relevant ultrasound data; and outputting, by the processor, to a display of the handheld ultrasound scanning device, a graphical representation representative of a result of the analysis.

Figure 9:
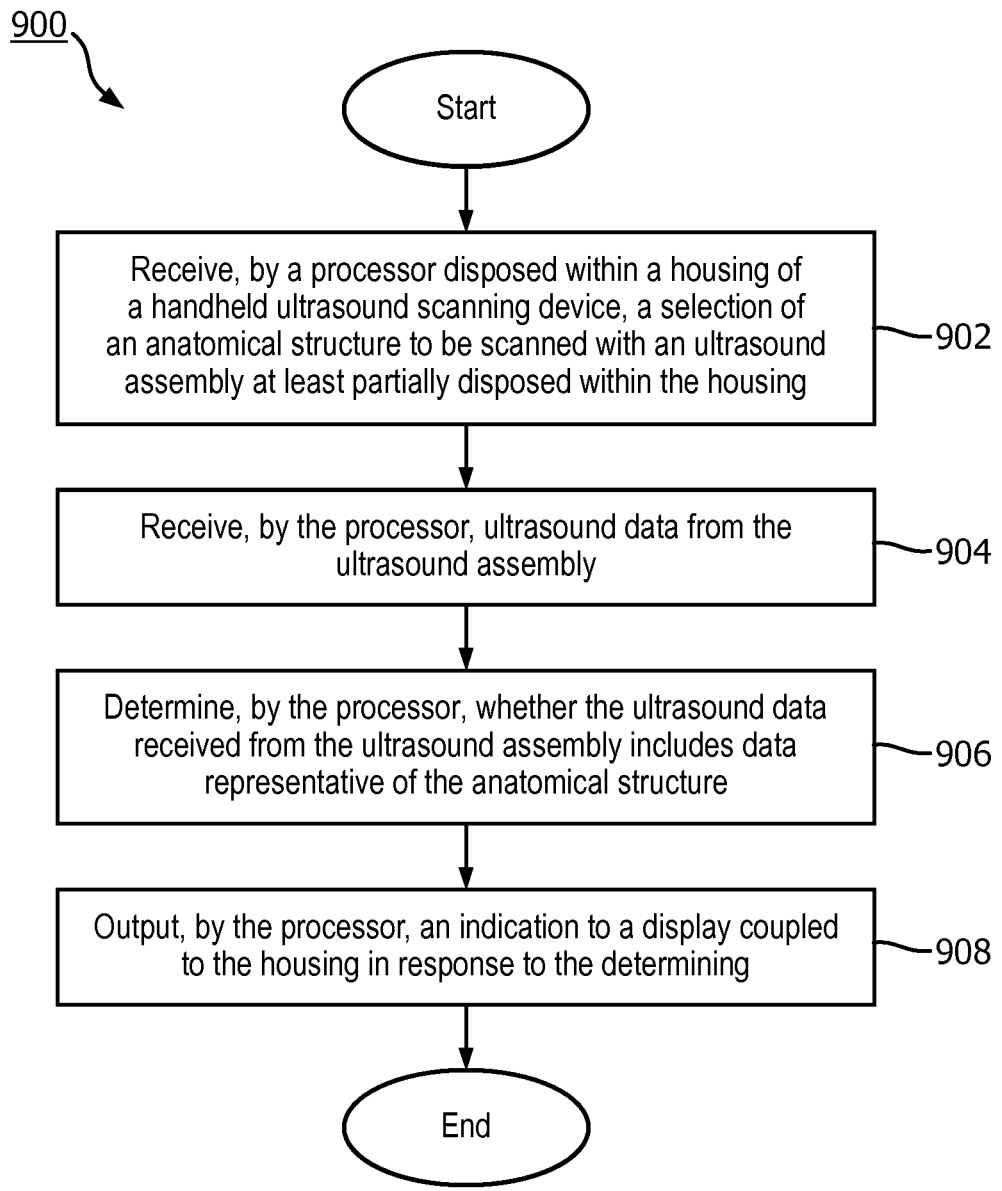
FIG. 9 is a flow chart of a method, according to aspects of the present disclosure.

Turning now to FIG. 9, a method 900 is described. The method 900 may be implemented by or with any of the handheld medical scanning devices described herein, e.g., handheld medical scanning devices 102, 202, 302, 402, 502, 602, and 702. The method begins at step 902 where a selection of an anatomical structure to be imaged with an ultrasound assembly at least partially disposed within a housing of a handheld ultrasound scanning device is received by a processor disposed within the housing. This step may also include the processor retrieving information of the anatomical structures to be selected from (such as imaging presets) prior to the user's selection. At step 904, the processor receives ultrasound data from the ultrasound assembly. The processor determines, at step 906, whether the ultrasound data received from the ultrasound assembly includes data representative of the anatomical structure. The processor outputs an indication to a display coupled to the housing of the handheld ultrasound scanning device in response to the determining at step 908. The method may further comprise communicating, by the processor, the received ultrasound data to a remote medical processing system. The received ultrasound data may be communicated to the remote medical processing system without an ultrasound image having been outputted to the display. The method may further comprise determining, by the processor, whether a scanning procedure has been completed; and outputting, by the processor, a second indication to the display in response to determining that the scanning procedure has been completed. The method may further comprise determining, by the processor, whether an assessment of the anatomical structure has been completed; and outputting, by the processor, a third indication to the display in response to determining that the assessment of the anatomical structure has been completed.

Aspects of the present disclosure advantageously provide feedback during ultrasound data acquisition and/or feedback relating ultrasound data assessment, without actually displaying an ultrasound image to the user of the device. In some instances, the feedback can be a graphical, visual, textual, numerical, and/or otherwise suitable representation presented on, e.g., an integrated display of the device. In some instances, the representation and/or the ultrasound image can be displayed on a remote display (e.g., spaced from the ultrasound scanning device). Other aspects of the present disclosure advantageously select and process only the most relevant ultrasound imaging data. For example, a processor of the ultrasound scanning device can make clinical measurements using the most relevant ultrasound imaging data. In some instances, a graphical, visual, textual, numerical, and/or otherwise suitable representation can displayed based on the processing. In some instances, the most relevant ultrasound images can be displayed, without displaying the other ultrasound images that were obtained. Providing a user, such as novice ultrasound operator or a patient, helpful direction during ultrasound data acquisition and/or output assessment of the obtained ultrasound data, without providing any ultrasound images or only a few selected ultrasound images advantageously minimizes the processing and memory hardware requirements for the ultrasound scanning device while still facilitating data acquisition/assessment workflow.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A handheld ultrasound scanning device, comprising:
a housing configured for handheld use;
an ultrasound imaging assembly at least partially disposed within the housing and configured to obtain ultrasound data;
a display unit at least partially disposed within the housing and comprising a display; and
a processor disposed within the housing, wherein the processor is in communication with the ultrasound imaging assembly and the display unit, the processor operable to:
receive a selection of an anatomical structure to be scanned with the ultrasound imaging assembly;
receive first ultrasound data from the ultrasound imaging assembly;
determine whether the first ultrasound data is representative of the anatomical structure; and
output, when the first ultrasound data is representative of the anatomical structure, a first indication to the display unit comprising a confirmation to the user that the positioning of the ultrasound imaging assembly is suitable for scanning the anatomical structure, wherein the first indication is displayed without any image of the anatomical structure while the ultrasound imaging assembly is obtaining the first ultrasound data, wherein the first indication is configured to provide guidance to a user for a positioning of the ultrasound imaging assembly; and receive, after outputting the first indication, second ultrasound data representative of the anatomical structure from the ultrasound imaging assembly, wherein the second ultrasound data is of a higher quality than the first ultrasound data.

2. The handheld ultrasound scanning device of claim 1, wherein the processor is further configured to:
output, when the first ultrasound data is not representative of the anatomical structure,
a third indication to the display comprising an alert to the user to change the positioning of the ultrasound imaging assembly to scan the anatomical structure.

3. The handheld ultrasound scanning device of claim 1, wherein the processor is further operable to output an audible tone in response to the determining.

4. The handheld ultrasound scanning device of claim 1, wherein the processor is further operable to:
communicate the second ultrasound data to a remote medical processing system.

5. The handheld ultrasound scanning device of claim 4, wherein the second ultrasound data is communicated to the remote medical processing system without an ultrasound image having been outputted to the display unit.

6. The handheld ultrasound scanning device of claim 4, wherein the processor is further operable to:
receive, from the remote medical processing system, an assessment result based on the second ultrasound data; and
output the assessment result to the display unit.

7. The handheld ultrasound scanning device of claim 1, wherein the processor is further operable to:
generate an assessment result based on the second ultrasound data; and
output the assessment result to the display unit.

8. The handheld ultrasound scanning device of claim 1, wherein the processor is further operable to:
determine whether a scanning procedure has been completed; and
output a fourth indication to the display unit in response to determining that the scanning procedure has been completed.

9. The handheld ultrasound scanning device of claim 8, wherein the processor is further operable to:
determine whether an assessment of the anatomical structure has been completed; and
output a fifth indication to the display unit in response to determining that the assessment of the anatomical structure has been completed.

10. The handheld ultrasound scanning device of claim 9, wherein the assessment of the anatomical structure comprises a measurement of the anatomical structure.

11. The handheld ultrasound scanning device of claim 1, wherein the ultrasound imaging assembly comprises a miniaturized ultrasound assembly comprising a micro-beamformer.

12. The handheld ultrasound scanning device of claim 1, wherein the first ultrasound data is more sparse than the second ultrasound data.

13. The handheld ultrasound scanning device of claim 1, wherein the first ultrasound data is collected across a first set of imaging planes,
wherein the second ultrasound data is collected across a second set of imaging planes, and
wherein the second set of imaging planes comprises a subset less than all of the first set of imaging planes.

14. The handheld ultrasound scanning device of claim 13, wherein the processor is further configured to generate the second set of imaging planes by determining the subset of imaging planes of the first set for receiving ultrasound data that is representative of the anatomical structure.

15. A method of ultrasound scanning, comprising:
receiving, by a processor disposed within a housing of a handheld ultrasound scanning device, a selection of an anatomical structure to be scanned with an ultrasound imaging assembly at least partially disposed within the housing;
receiving, by the processor, first ultrasound data from the ultrasound imaging assembly;
determining, by the processor, whether the first ultrasound data is representative of the anatomical structure; and
outputting, by the processor, when the first ultrasound data is representative of the anatomical structure, a first indication to a display unit comprising a confirmation to the user that the positioning of the ultrasound imaging assembly is suitable for scanning the anatomical structure, wherein the display unit is at least partially disposed in the housing and comprises a display, wherein the first indication is displayed without any image of the anatomical structure while the ultrasound imaging assembly is obtaining the first ultrasound data, wherein the first indication is configured to provide guidance to a user for a positioning of the ultrasound imaging assembly; and
receiving, after outputting the first indication, second ultrasound data representative of the anatomical structure from the ultrasound imaging assembly, wherein the second ultrasound data is of a higher quality than the first ultrasound data.

16. The method of claim 15, further comprising
communicating, by the processor, the second ultrasound data to a remote medical processing system.

17. The method of claim 16, wherein the second ultrasound data is communicated to the remote medical processing system without an ultrasound image having been outputted to the display unit.

18. The method of claim 15, further comprising:
determining, by the processor, whether a scanning procedure has been completed; and
outputting, by the processor, a third indication to the display unit in response to determining that the scanning procedure has been completed.

19. The method of claim 18, further comprising:
determining, by the processor, whether an assessment of the anatomical structure has been completed; and
outputting, by the processor, a fourth indication to the display unit in response to determining that the assessment of the anatomical structure has been completed.

20. The method of claim 15, wherein:
the first ultrasound data is collected across a first set of imaging planes; and
the second ultrasound data is collected across a second set of imaging planes, the second set of imaging planes comprising a subset less than all of the first set of imaging planes.

* * * * *